United States Patent [19]

Skakoon et al.

[11] Patent Number: 4,544,369
[45] Date of Patent: Oct. 1, 1985

[54] BATTERY OPERATED MINIATURE SYRINGE INFUSION PUMP

[75] Inventors: James G. Skakoon, Norwood; Donald L. Johanson, Wayland, both of Mass.; Raymond J. Bonthron, New Providence, N.J.

[73] Assignee: C. R. Bard, Inc., Murray Hill, N.J.

[21] Appl. No.: 554,368

[22] Filed: Nov. 22, 1983

[51] Int. Cl.⁴ .............................. A61M 5/20
[52] U.S. Cl. ...................... 604/155; 604/245; 128/DIG. 12
[58] Field of Search ........... 604/155, 154, 131, 245; 128/DIG. 1, DIG. 12

[56] References Cited

U.S. PATENT DOCUMENTS

| | | | |
|---|---|---|---|
| 3,336,925 | 8/1967 | Thompson III | 604/155 |
| 3,415,419 | 12/1968 | Jewitt et al. | 604/155 X |
| 3,456,649 | 7/1969 | Jewitt | 604/155 |
| 4,191,187 | 3/1980 | Wright | 604/155 |
| 4,424,720 | 1/1984 | Bucchianeri | 604/155 |
| 4,435,173 | 3/1984 | Siposs et al. | 604/155 |
| 4,465,474 | 8/1984 | Mardorf et al. | 604/154 |

Primary Examiner—Stephen C. Pellegrino
Attorney, Agent, or Firm—Kane, Dalsimer, Kane, Sullivan and Kurucz

[57] ABSTRACT

A small, light weight, battery operated, fixed speed syringe infusion pump is capable of being IV pole mounted. A disposable syringe is secured in a snap-in holder and the syringe plunger is moved by a pusher. The pusher is advanced to the syringe plunger by squeezing a finger tab. This simultaneously decouples the pusher from the internal drive and opens the antisiphon catch to allow quick and easy set-up. To initiate flow, a switch is moved to the "on" position. The pusher is moved by the engagement of a nut on a threaded lead screw. The lead screw is rotated, through appropriate gearing, by a direct current motor. A force sensing system is included as part of the syringe holder and is used to detect end of syringe and occlusion. Visual indicators and audio alarms for infusion and warning and to sense condition of the batteries are provided.

15 Claims, 12 Drawing Figures

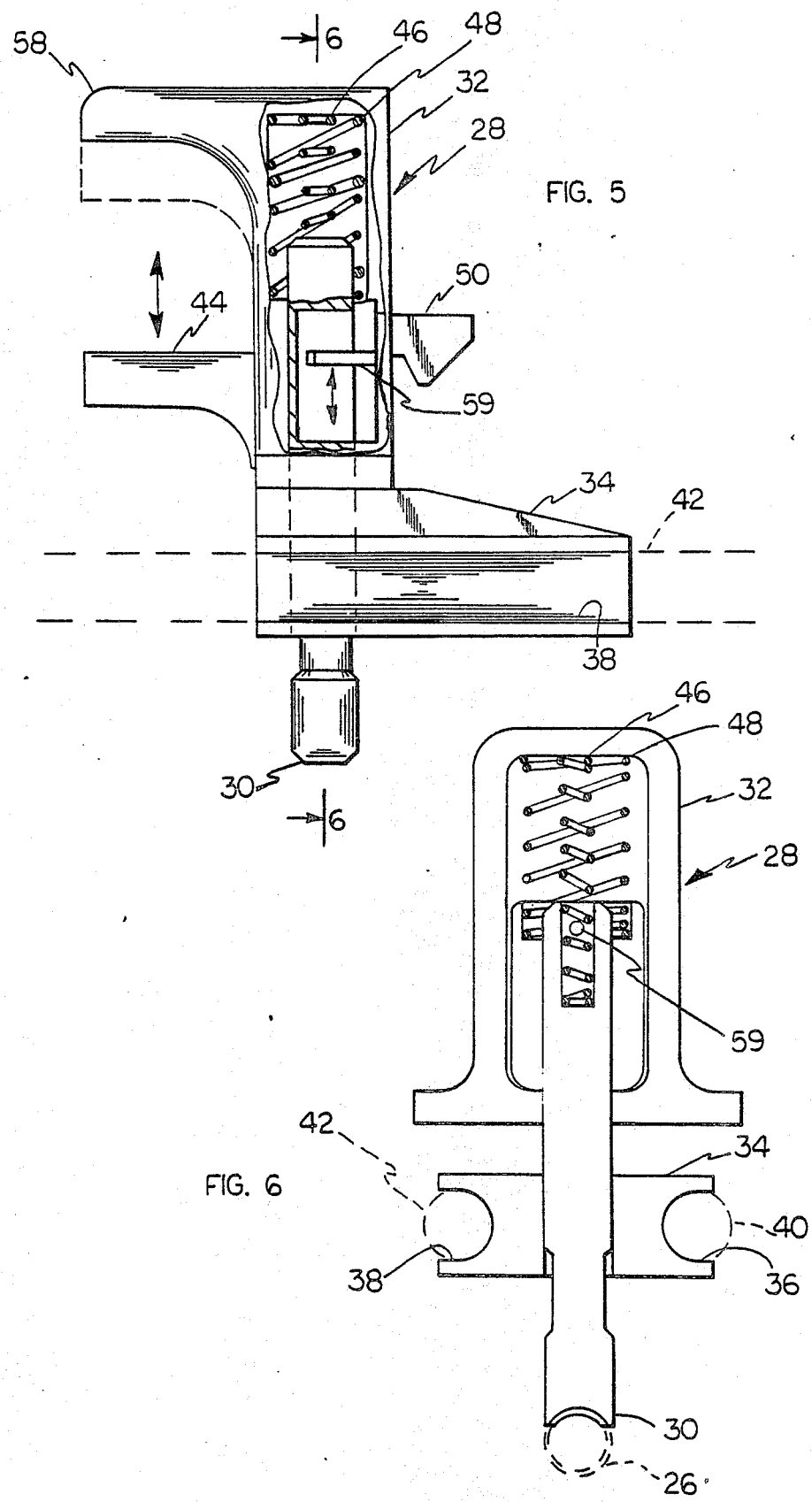

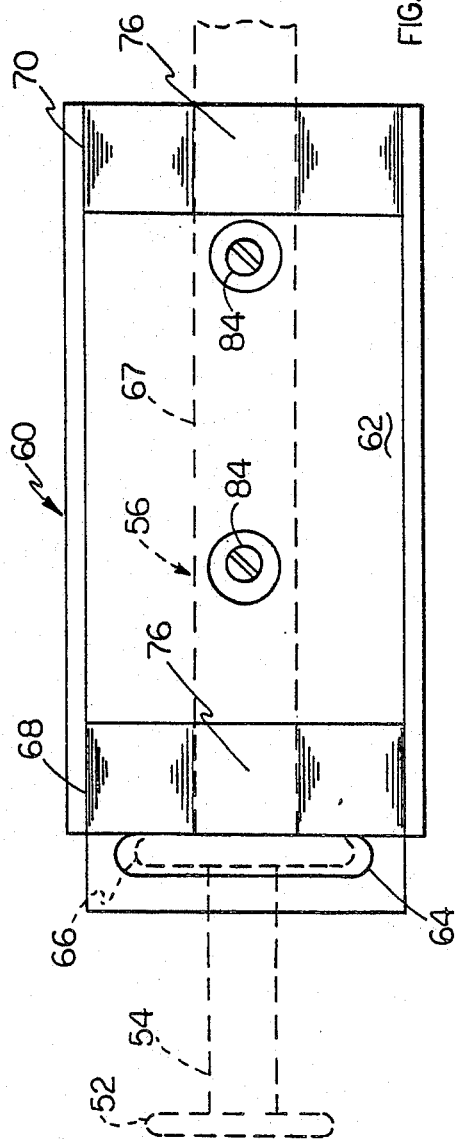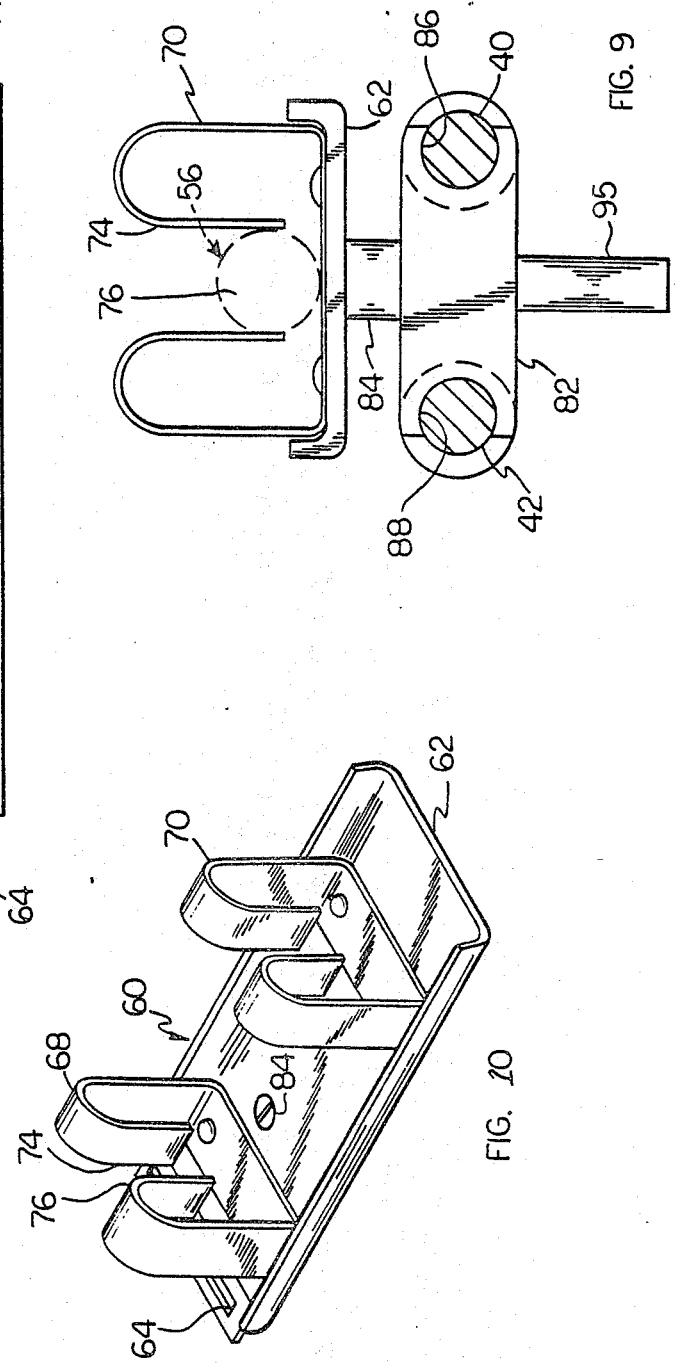

BATTERY OPERATED MINIATURE SYRINGE INFUSION PUMP

BACKGROUND OF THE INVENTION

There is an ever increasing acceptance and use of infusion pumps for drug and medicament administration. However, there has developed a need for a light weight, small and portable syringe infusion pump that is battery operated which may be readily attached to or hung from an IV pole or used for ambulatory patients. Needless to say, this infusion pump should be safe and reliable for administering dosages over a wide range of dosage times without severe restriction as to syringe supplier or manufacturer while possessing ultimate simplicity of operation and economy of manufacture.

SUMMARY OF THE INVENTION

It is therefore a principal object of the present invention to satisfy the foregoing need by providing a fixed or multiple syringe infusion pump for reliable and accurate intravenous administration of therapeutic agents and drugs such as antibiotics. Towards this end, the syringe infusion pump incorporating the teachings of this invention is relatively small, light weight and battery operated, so that it can be easily and readily attached to or hung from an IV pole. In this manner, the infusion may be directly into a patient's vein, similar to present antibiotic infusion methods or convenient Y-site piggybacking of an existing IV infusion.

Another principal object is to provide an infusion pump that will accept essentially most plastic disposable syringes from the various syringe manufacturers. Inasmuch as the pump possesses a single fixed speed, and accommodates this wide variety of syringes, the rate of delivery is indicated by a time scale showing the time remaining to complete the emptying of the syringe.

A further object is to provide a syringe infusion pump with a pusher block system incorporating an antisiphon capability and drive decoupling with a simple manipulative step and motion that permits set up of a syringe in the pump notwithstanding the variety of syringe sizes that may be accommodated.

Another important object is to provide a syringe infusion pump of the foregoing type that is capable of sensing either an end of syringe or overpressure such as caused by occlusion.

A further important object is to provide a syringe infusion pump of the foregoing type possessing visual indicator during infusion, completion of the dose and when occlusion or overpressure may occur. An optional audio alarm may be selected as an indicator of the end of syringe or at occlusion. In either event the syringe pump will terminate infusion which may be resumed only upon correction of the condition and thereafter deliberately restarting the infusion cycle. A low battery light is displayed when the batteries require replacement, however, allowing for a time of continuous use after the first display sufficiently long to complete a number of infusion cycles.

In general, the infusion pump of this invention will hold and empty a syringe at a constant continuous rate. The syringe barrel is secured in a snap-in holder and the syringe plunger is moved by a pusher. The pusher is advanced to the syringe plunger during set-up by squeezing a finger tab and sliding the pusher forward. This simultaneously decouples the pusher from the internal drive and opens the antisiphon catch to allow quick and easy set-up. To initiate flow, a switch moved to the "on" position. The pusher is moved by th engagement of a nut on a threaded lead screw. The lea screw is rotated, through appropriate gearing, by direct current motor. A force sensing system is include as part of the syringe holder and is used to detect end c syringe and occlusion. Visual indicators and audi alarms for infusion and warning and to sense conditio of the batteries are provided.

Other objects and advantages will become apparer from the following detailed description which is to b taken in conjunction with the accompanying drawing:

BRIEF DESCRIPTION OF THE DRAWINGS

In the drawings:

FIG. 5 is an enlarged side elevational view of th pusher block assembly with certain parts broken awa and removed and sectioned;

FIG. 6 is a sectional view taken along the line 6—6 c FIG. 5;

FIG. 8 is a top plan view of the syringe holder;

FIG. 9 is an end view thereof showing its connectio with the end of syringe and overpressure assembly;

FIG. 10 is a perspective view of the syringe holdei

DETAILED DESCRIPTION

Figure 1:
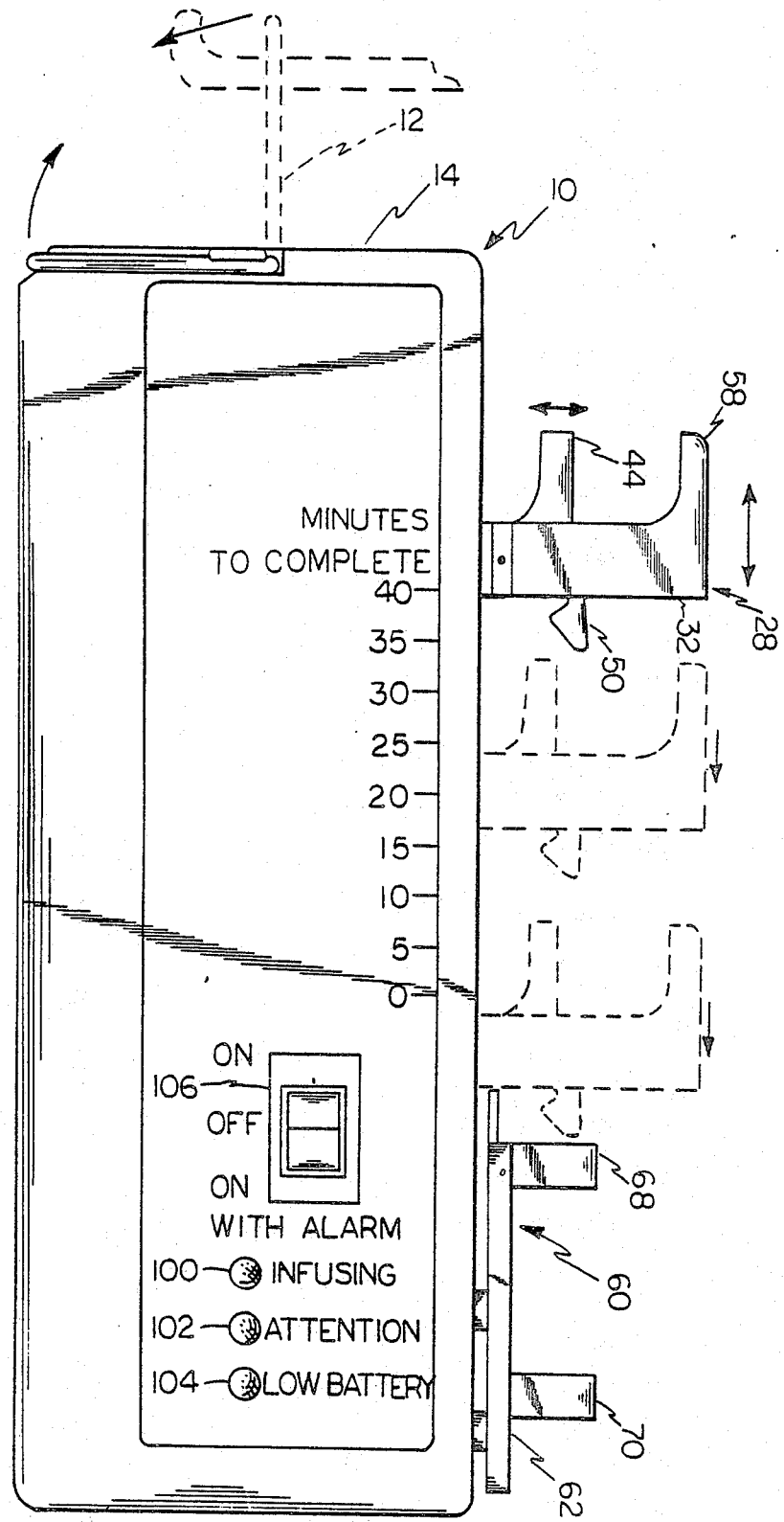
FIG. 1 is a front elevational view of a battery opei ated syringe infusion pump of this invention.
Figure 2:
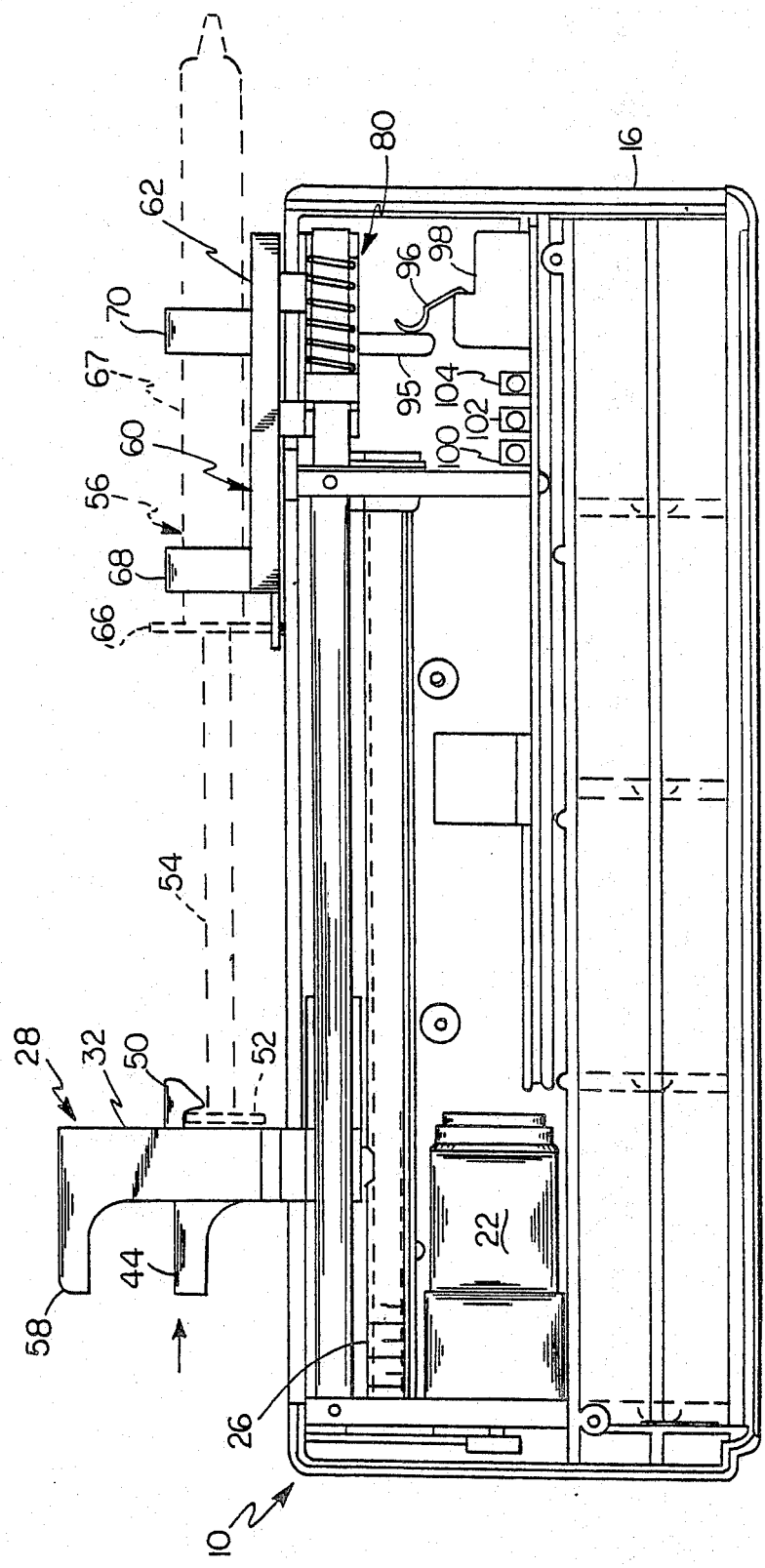
FIG. 2 is a similar front elevational view with th front cover removed.
Figure 4:
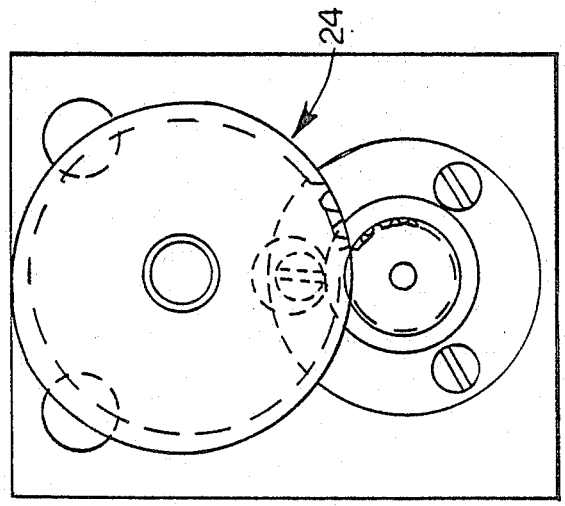
FIG. 4 is an end view of motor gear drive for the lea screw.
Figure 3:
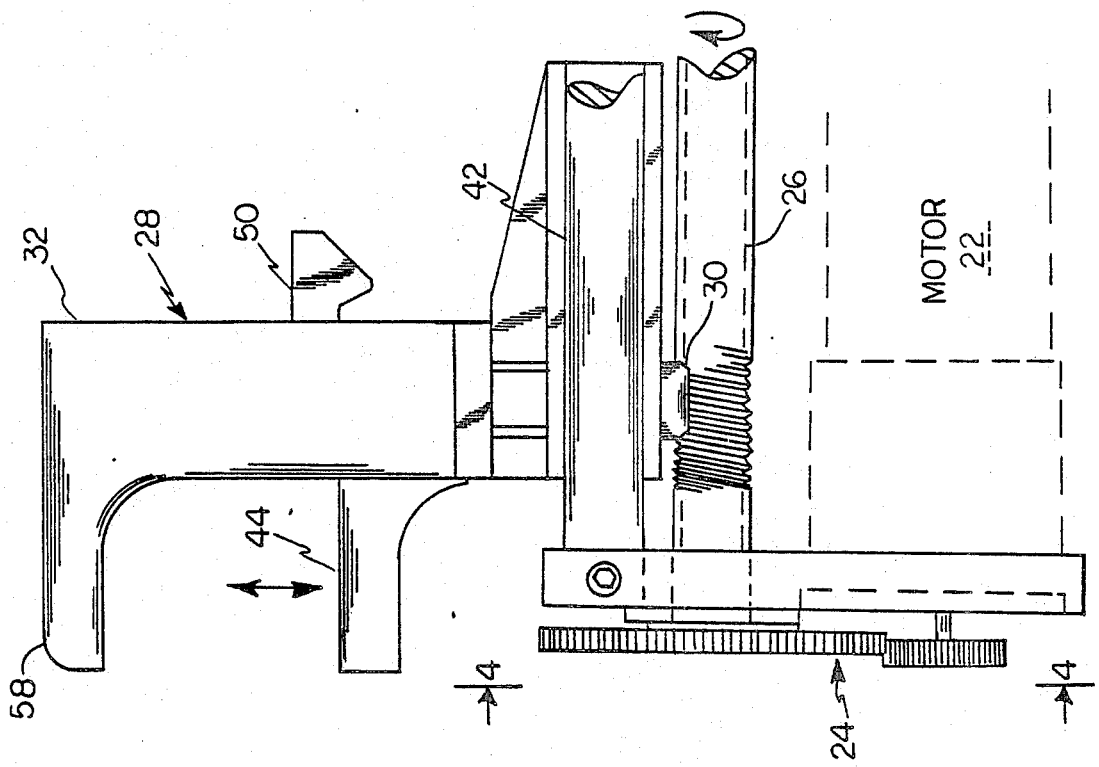
FIG. 3 is an enlarged fragmentary view of the pushe block assembly shown associated with the lead screw
Figure 7:
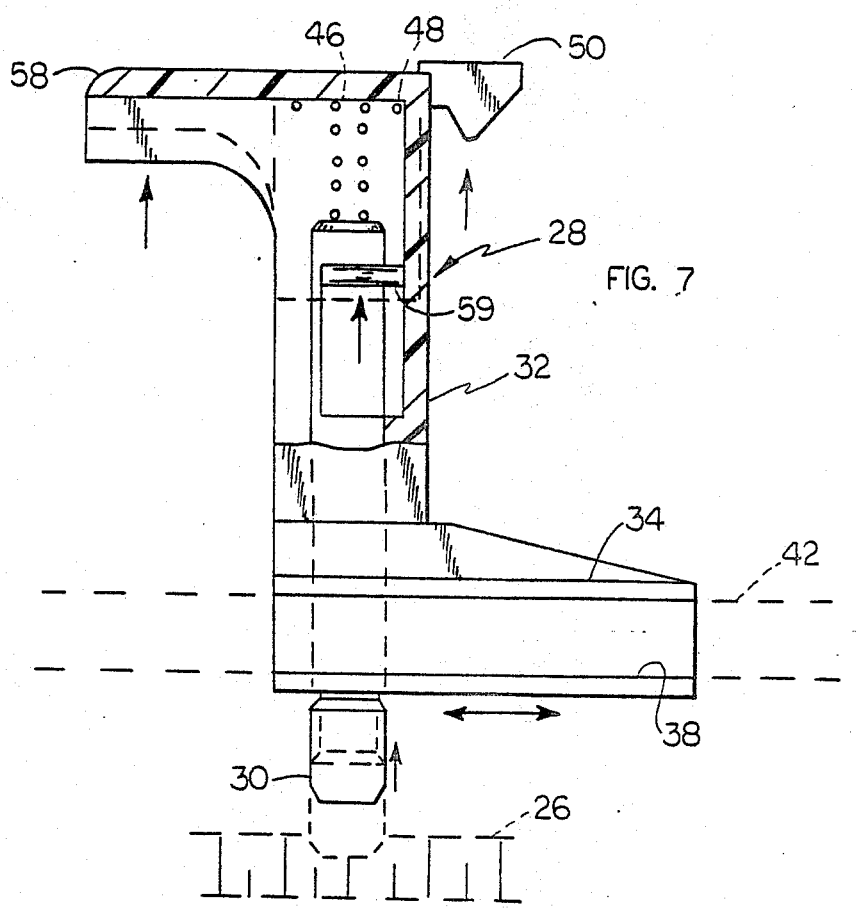
FIG. 7 is another enlarged side elevational view c the pusher block assembly showing the disengagemer of the lead screw.
Figure 11:
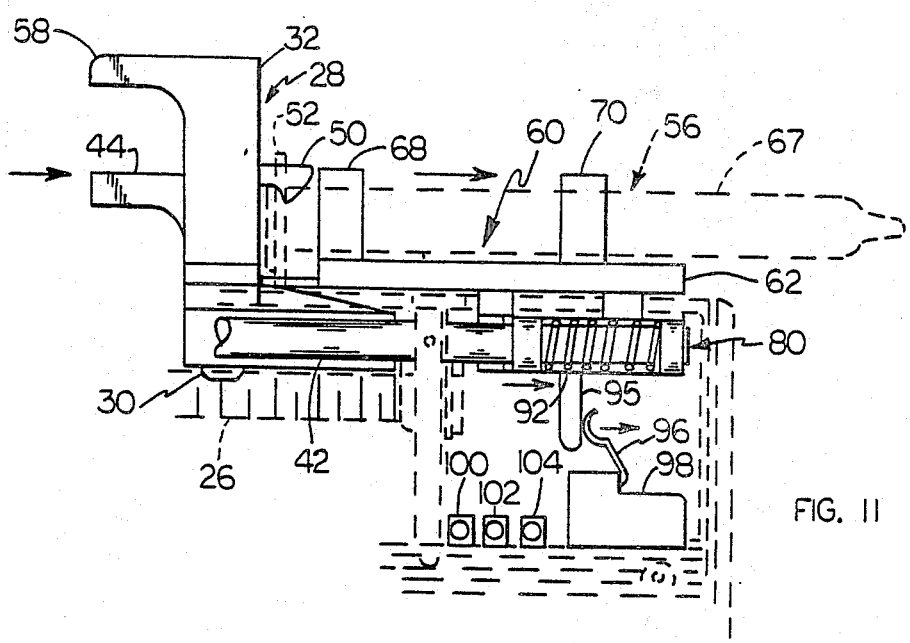
FIG. 11 is a side fragmentary side elevational view c the pusher block assembly, syringe holder and assoc ated end of syringe and overpressure assembly.
Figure 12:
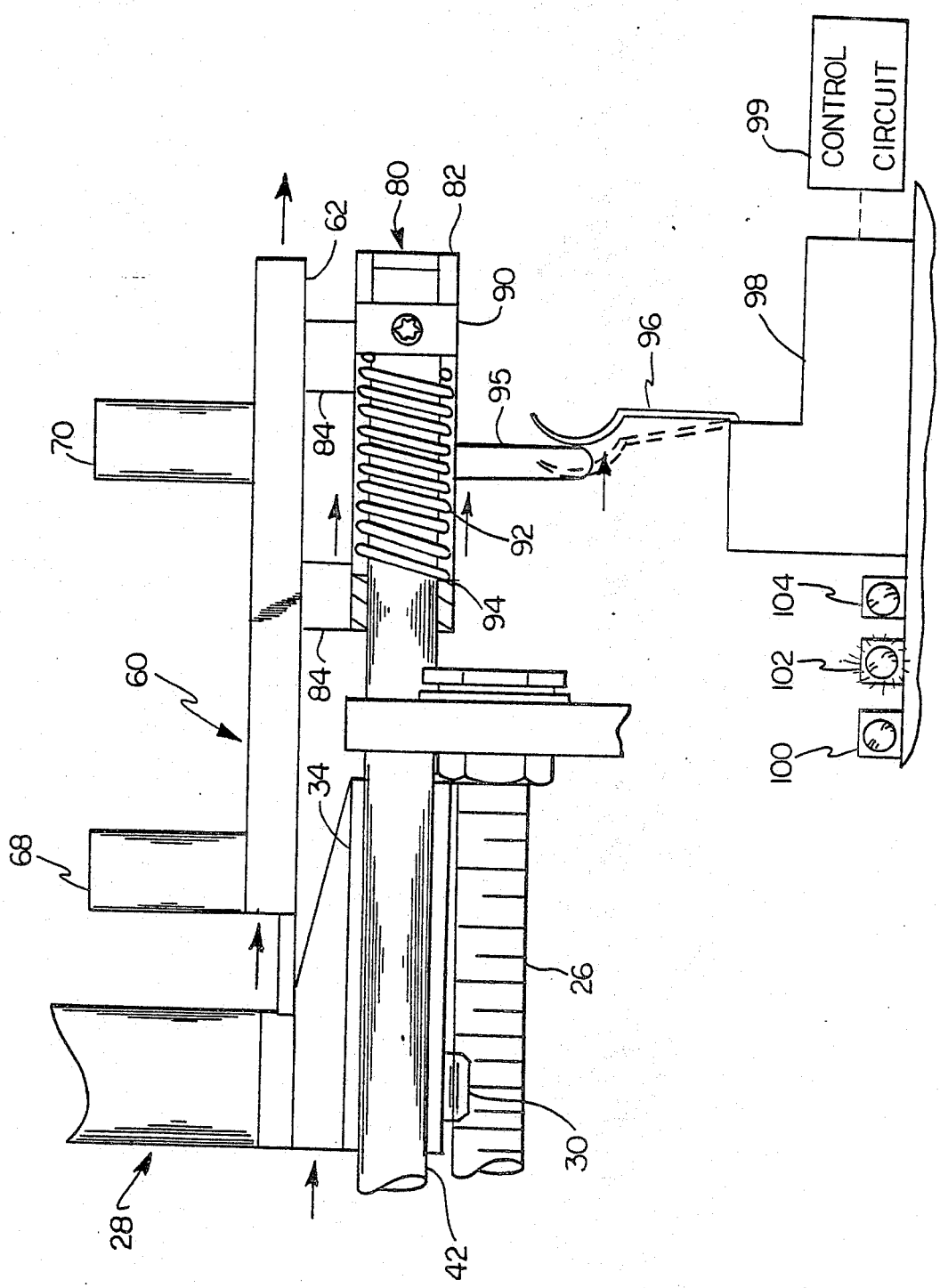
FIG. 12 is a further enlarged fragmentary view of tł end of syringe and overpressure assembly showing a( tuation of the alarm switch.

In the drawings, a small, light weight battery ope ated syringe infusion pump 10 of this invention adapted to be hung or suspended from an IV pole c similar conveniently located support by means of a tachment loop 12, pivotal between a retracted positic and an extended position as shown in FIG. 1. A froi cover 14 and a rear cover 16 advantageously houses tł internal componentry and defines compartment 18 thi conveniently receives the batteries 20 for energizing tł fixed and single or multiple speed motor 22. The driv of motor 22 is coupled with gear network 24 which i turn drives the lead screw 26 in a manner well known i the art.

A pusher block assembly 28 is provided with a driv half-nut 30 which advantageously engages with the lea screw 26. The assembly also selectively engages wit the rear end of the syringe plunger for expelling an discharge of the syringe contents at a fixed rat Towards this end, the pusher block assembly includes block 32 that has a bottom end 34 provided with a pa of channels 36 and 38 that receive guide rods 40 and 4: respectively, which cooperate in causing the pushe block assembly 28 to move forwardly upon turning c the lead screw 26 as a result of the meshing therewith b the drive half-nut 30. A lever 44 rides in the block and axially on the upper end of the drive nut 30. The spring 46 provides the force to cause engagement of the drive nut 30 with lead screw 26. Spring 48 on the other hand provides the force to keep lever 44, and particularly antisiphon catch 50 engaged with flange 52 of plunger 54 of syringe 56. In this manner escape of plunger 54 is prevented which otherwise could result in a siphoning action.

The pusher block assembly 28 may be moved by squeezing lever 44 towards the upper laterally extending leg 58 of the block 32. This will permit the syringe plunger flange 52 to be immediately released or permit the flange of a fresh syringe 56 to be engaged by the pusher block 28. As this motion is continued, pin 59 extending laterally from the drive nut 30 will be engaged by lever 44 lifting drive nut 30 away from the lead screw 26 to effect drive decoupling. The pusher block assembly 28 may then be freely moved along the guide rails 40, 42 for removal of a spent or emptied syringe 56 or reengagement by catch 50 of another flange 52 of a fresh filled syringe 56. Thus, release of the lever 44 causes immediately reengagement of the drive nut 30 with the lead screw 26. As the motion of the lever 44 is continued, the antisiphon catch 50 engages with the syringe plunger flange 52. Accordingly, with the same action coupling of the drive nut and antisiphoning is accomplished to thereby facilitate proper positioning of the syringe, pusher block and antisiphon mechanism one with the other. Furthermore, the antisiphon mechanism is designed to accept and capture a variety of syringe plunger flange sizes by allowing it to move to a capturing position independent of the drive nut engagement position.

The syringe holder 60 advantageously permits the utilization of a wide variety of disposable syringes from various syringe manufacturers. In this connection, a syringe holder 60 is provided with a base 62 connected with an end of syringe and overpressure assembly to be described in detail shortly. The base 62 is provided with an elongated slot 64 which conveniently receives the rear flange 66 of the syringe barrel 67. A pair of spring clips 68 are riveted or otherwise connected with the base 62. Each clip includes a pair of spaced upwardly extending legs 72 which are bent downwardly to form the downwardly depending arm 74 that defines with the oppositely spaced arm an opening 76 for the reception of a syringe barrel 67. In view of the flexure of the legs and the arms 74, various size syringes may be accommodated notwithstanding the manufacturer.

Reference is now made to the end of syringe and an overpressure sensing assembly 80 which permits the generation of a suitable signal when the contents of the syringe 56 has been fully discharged or an occlusion or other situation that would cause over pressure in the discharge line has occurred. The system 80 includes a block 82 which is rigidly connected wiht the syringe holder base 62 by interconnecting pins 84. Block 82 is provided with accommodating recesses 86 and 88 which receive the forward end of guide rods 40 and 42. A collar 90 is fixed to the rod 42 and a preload spring 92 interposed between this collar 90 and shoulder 94 on the block 82 provides a fixed normal position for this block 82 and consequently the syringe holder base 62. The preload force provided by the spring 92 must be overcome by the syringe holder 60 in order to move the arm 96 of the switch 98. Actuation of the switch 98 will provide an electrical outlet to the control circuit 96 as needed either to activate a visual or audible alarm. As explained the preload force provided by the spring 92 will be overcome by either of the following events. Firstly, plunger 54 may bottom out in the syringe barrel 55 causing the drive nut 30 to provide the overcoming force. Secondly, the discharge from the syringe barrel 67 may be occluded or partially occluded so that pressure increases inside the barrel 67 as the drive nut 30 moves forward. This pressure will provide a counter force to again cause the drive nut to provide the overcoming force to move the syringe holder 60 in a forward direction so that arm 95 extending downwardly from the block 82 will move the arm 96 to thereby activate the switch 98.

In use, a filled syringe with the selected drug or medicament is attached to the syringe holder 60 with the barrel 55 disposed between the clips 68 and 70 and the barrel flange 66 in the slot 64. The pusher block assembly 28 is moved forwardly upon lifting of lever 44 fully towards the leg 58 of the block 32. When the flange 52 of the plunger 54 is encountered the lever 44 is released to cause the drive nut 30 to reengage with the lead screw 26 and the catch 50 captures the flange 52. Knowing the fixed constant speed of the infusion pump 10 and knowing syringe size and the contained volume, the flow rate and time of delivery may be calculated or taken from appropriately prepared charts or nomographs. The infusion pump 10 may be suspended from an IV pole and the tubing from the syringe can be connected to the appropriate infusion site which may be a primary administration set.

As shown in FIG. 1 of the drawings, a visual display may be provided for normal infusion operation 100, end of syringe or occlusion 102 and low battery 104. A conveniently located on-off switch 106 may be of the double acting type to provide simple visual indication or visual coupled with audible, and, in particular with an occlusion alarm 108.

In a successful application of the present invention the infusion pump 10 possessed a size of 8.5 inches by 4.5 inches by 1.6 inches and a weight of 1 lb. 12 oz and used C-size alkaline batteries. One embodiment accepted disposable syringes from several manufacturers ranging in size from 3-12 milliliters while another accepted syringes from 20-60 milliliters and a third accepted syringes from 10-35 milliliters.

Thus the several aforenoted objects and advantages are most effectively attained. Although a single somewhat preferred embodiment of the invention has been disclosed and described in detail herein, it should be understood that this invention is in no sense limited thereby and its scope is to be determined by that of the appended claims.

What is claimed is:

1. A syringe infusion pump comprising:
   a casing;
   a motor supported by the casing;
   electronic means for controlling the motor;
   battery means in the casing for energizing the motor;
   a lead screw supported on the casing and rotatably coupled with the motor;
   support means on the casing for supporting a syringe having a cylinder and piston, the support means including acceptance means for accepting syringes from various syringe manufactures, the support means including a base provided with a slot for receiving the flange of a syringe cylinder for preventing reverse longitudinal movement thereof so that longitudinal movement of the cylinder will be transmitted to the base, and spring means within the casing cooperating with the base to bias the base and adapted to be overcome by movement of the flange and base, said acceptance means including a base, a pair of upstanding laterally flexible clips on the base receiving the syringes; and coupling means for coupling the piston with the lead screw for driving the piston into the cylinder upon rotation of the lead screw.

2. The invention in accordance with claim 1, wherein the pump is miniaturized, light weight and portable with hanging means on the casing for hanging the pump from an IV pole.

3. The invention in accordance with claim 1, wherein each clip includes a pair of spaced upstanding flexible legs each being provided with bend at the upper end thereof to form a downwardly depending flexible arm for engaging the exterior of the syringe cylinder.

4. A syringe infusion pump comprising:
a casing;
a motor supported by the casing;
electronic means for controlling the motor;
battery means in the casing for energizing the motor;
a lead screw supported on the casing and rotatably coupled with the rotor;
support means on the casing for supporting a syringe having a cylinder and piston, the support means including acceptance means for accepting syringes from various syringe manufacturers, said acceptance means including a base, a pair of upstanding laterally flexible clips on the base receiving the syringes;
coupling means for coupling the piston with the lead screw for driving the piston into the cylinder upon rotation of the lead screw;
the support means being mounted for limited longitudinal movement from a first predetermined position to a second predetermined position;
spring means within the casing for urging the support means towards the first predetermined position;
a switch means proximate the support means; and
single sensing means for actuating the switch means upon sensing the bottom of the plunger in the syringe and the end of the injection cycle and sensing overpressure of the injection network from the syringe to the patient when said syringe overcomes the spring means and urges the syringe holder towards the second position.

5. The invention in accordance with claim 4, wherein an antisiphon and drive decoupling means is movable between a retracted position at which it is decoupled with the drive means and at the same time disengages with the plunger of the syringe and a forward position at which it couples with the drive means and at the same time engages with the plunger of syringe to prevent escape of the plunger and consequent siphoning action by the syringe.

6. A syringe infusion pump comprising: support means; means for driving a syringe plunger on the support means;

a syringe holder mounted for limited longitudinal movement on the support means from a first predetermined position to a second predetermined position;
spring means for urging the holder towards the first predetermined position;
a switch means proximate the syringe holder; and
single sensing means for actuating the switch mea upon sensing the bottom of the plunger in the s ringe and the end of the injection cycle and sensi overpressure of the injection network from t syringe to the patient means and the syringe hold towards the second position;
a pair of spaced longitudinally extending rails on t support means, the syringe holder includes a blo slidably mounted on the rails, a stop on one of t rails at the second position, and the means being spring on said one rail engaged at one end with t stop and the other end with the block biasing t block towards the first predetermined position.

7. The invention in accordance with claim 6, where the switch is coupled with an alarm adapted to be e gaged upon actuation of the switch means.

8. The invention in accordance with claim 6, where the holder includes a base connected with the block pair of upstanding laterally flexible clips on the base receiving and accepting syringes from various syrin manufacturers.

9. The invention in accordance with claim 8, where the syringe includes a piston slidable in a cylinder ha ing a rear flange, and the base is provided with a slot receiving the flange of a syringe cylinder preventi reverse longitudinal movement thereof so that longi dinal movement of the cylinder will be transmitted the base, and the spring means cooperating with t base to bias the base and adapted to be overcome movement of the flange and base.

10. The invention in accordance with claim wherein each clip includes a pair of spaced upstandi flexible legs each being provided with bend at the up end thereof to form a downwardly depending flexi arm for engaging the exterior of the syringe cylinde 11. A syringe infusion pump comprising;
a support;
a syringe holder on the support;
drive means on the support for driving the syrin plunger into the syringe barrel;
an antisiphon and drive decoupling means on t support movable between a retracted position which it is decoupled with the drive means and the same time disengages with the plunger of t syringe and a forward position at which it coup with the drive means and substantially shor thereafter engages with the plunger of syringe prevent escape of the plunger and consequent phoning action by the syringe, the antisiphoni and drive decoupling means including a pusl block slidable longitudinally on the support, a le on the block having a plunger flange engag surface, a drive means engaging surface on block for meshing with the drive means, the le being shiftable between the retracted position a the forward position, the drive means engag surface being shiftable between the retracted p tion and the forward position.

12. The invention in accordance with claim wherein the drive means includes a rotatably dri lead screw on the support, and the drive means eng ing surface is a half nut on a post that is axially recip cal in the block, first biasing means for urging the into the forward position at which the half nut mes with the lead screw.

13. The invention in accordance with claim wherein second biasing means urges the lever towa the forward position at which the plunger flange eng ing surface engages with a plunger flange of a syringe in the syringe holder.

14. The invention in accordance with claim 13, wherein the lever is manually slidable in the block from the forward position to the retracted position against the bias of the first biasing means and interengaging surface means between the block and the post that interengage against the bias of the second biasing means when the lever approaches the retracted position to cause the post to retract to disengage the half nut from the lead screw and that disengage when the lever is released to cause the post to slide forwardly to engage the half nut and the lead screw prior to engagement of the flange engaging surface with the plunger flange to prevent siphoning action by the syringe.

15. The invention in accordance with claim 11, wherein a pair of spaced longitudinally extending guide rails are on the support, the pusher block being slidable on the guide rails, and separate means on the block for coupling with the drive means and in timed fashion with the plunger.

* * * * *

UNITED STATES PATENT AND TRADEMARK OFFICE
CERTIFICATE OF CORRECTION

PATENT NO. : 4,544,369

DATED : October 1, 1985

INVENTOR(S) : JAMES G. SKAKOON et al.

It is certified that error appears in the above-identified patent and that said Letters Patent is hereby corrected as shown below:

In column 3, line 48 after "legs" insert --72--.

In column 3, line 57 change "wiht" to --with--.

In claim 6, line 15 after "patient" insert --when said syringe overcomes the spring-- and after "and" insert urges--.

Signed and Sealed this

Nineteenth Day of August 1986

[SEAL]

*Attest:*

DONALD J. QUIGG

*Attesting Officer*

*Commissioner of Patents and Trademarks*